US00PP11589P

United States Patent [19]

Boeder

[11] Patent Number: Plant 11,589

[45] Date of Patent: Oct. 24, 2000

[54] CHRYSANTHEMUM PLANT NAMED 'BRONZE DISCO TIME'

[75] Inventor: Mark Boeder, West Wittering, United Kingdom

[73] Assignee: Cleangro Limited, United Kingdom

[21] Appl. No.: 09/189,713

[22] Filed: Nov. 11, 1998

[51] Int. Cl.[7] ..... A01H 5/00

[52] U.S. Cl. ..... Plt./296

[58] Field of Search ..... Plt./295, 296

*Primary Examiner*—Howard J. Locker
*Attorney, Agent, or Firm*—Christie, Parker & Hale, LLP

[57] ABSTRACT

A new variety of chrysanthemum producing golden orange flowers.

1 Drawing Sheet

BACKGROUND OF THE INVENTION

The present invention is directed to a new and distinct variety of chrysanthemum botanically classified as *Dendranthema grandiflora*. The varietal denomination of the new chrysanthemum is 'Bronze Disco Time'.

The new variety was discovered as a naturally occurring whole plant mutation in a cultivated planting of the variety 'Disco Time'. The new variety has been asexually reproduced by vegetative cuttings in Ventura County, Calif. and the distinguishing characteristics are retained through successive generations of asexual reproduction.

SUMMARY OF THE INVENTION

'Bronze Disco Time' is a crysanthemum plant variety that produces daisy-type golden orange flowers on a plant suitable for pot mum production and can be produced as a spray or disbud crop.

COMPARISON WITH PARENT

Flowers of the new variety are golden orange and flowers of the parent 'Disco Time' are pale apricot.

BRIEF DESCRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of April. 'Bronze Disco Time' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. It has been observed that the life of individual blooms of 'Bronze Disco Time' is about 21 days with the response time of about 8 weeks. One treatment with growth regulator B9 at 2000 ppm is useful. Desirable growing conditions include average night temperatures of about 65° and day temperatures of about 750–850° at about 5000–6000 foot candles.

Plant:
- *Habit.*—Upright.
- *Height.*—About 29 cm after application as described.
- *Number of breaks from pinch.*—About 4 to 5.
- *Length of lateral branches.*—About 22 cm.
- *Stem color.*—Near 137C.

Foliage:
- *Leaf arrangement.*—Alternate.
- *Number of leaves per lateral branch.*—About 9 fully expanded leaves.
- *Leaf size.*—Length: About 9 cm. Width: About 4.7 cm.
- *Leaf shape.*—Ovate.
- *Attachment.*—Petioled.
- *Leaf apex.*—Mucronate.
- *Base.*—Attenuate.
- *Margin.*—Lobed, infrequent serrations.
- *Aspect.*—Undulating.
- *Surface.*—Top: Slightly pubescent. Bottom: Pubescent.
- *Venation color.*—Underside: Near 146B. Upperside: Near 137D.
- *Petiole.*—Length: About 2.4 cm. Color: Near 146B.
- *Color.*—Mature leaf: Top: Near 137A. Underside: Near 137C. Young leaf: Top: Near 137A. Underside: Near 137C.

Flower:
- *Inflorescence form.*—Cyme.
- *Flower type.*—Daisy.
- *Number of blooms per branch.*—About 7.
- *Diameter of fully expanded bloom.*—About 8.1 cm.
- *Diameter of disc.*—About 1.5 cm.
- *Depth of fully expanded bloom.*—About 2.8 cm.
- *Sepal number.*—About 30. Color: Near 137B. Length: About 1 cm. General appearance: Pubescent.
- *Peduncle.*—Length: Uppermost peduncle: About 6 cm. Lateral peduncle: About 7.8 cm. Aspect: Straight. Surface: Pubescent. Strength: Sturdy.
- *Flower bud shape.*—Flattened sphere. Diameter About 1 cm. Height: About 0.6 cm.
- *Ray florets.*—Number per flower: About 20. Shape: Oblanceolate. Apex: Obtuse. Base: Tapered. Margin: Entire. Aspect: Undulating. Length: About 4.9 cm. Width: About 1.4 cm.
- *Disc florets.*—Number per flower: About 210. Shape: Cylindric. Margin: Entire. Length: About 0.5 cm. Width: About 0.1 cm.
- *Fragrance.*—Very faint.

Flower color:
- *General flower coloration.*—Golden orange, daisy-type with yellow disc; center of disc is green.

*Ray florets, top side.*—Immature: Near 26A. Mature: Near 24B. Fading: Near 23B.

*Ray florets, under side.*—Immature: Near 26B. Mature: Near 22B. Fading: Near 21D.

*Disc florets.*—Immature: Near 154B. Mature: Near 15A. Fading: Near 17C.

*Changes as the flower ages.*—Disc turns from yellow-green to yellow; flower form becomes more flat.

Reproductive organs:

*Ray florets.*—Pistillate. Stigma shape: 2 branched. Stigma color: Near 13B. Style length: About 0.5 cm.

*Disc florets.*—Complete. Stigma shape: 2 branched. Stigma color: Near 14B. Style Length: About 0.4 cm. Stamen number: About 5. Anther length: About 0.2 cm. Pollen color: Near 14A. Pollen quantity: Scarce.

What is claimed is:

1. A new and distinct chrysanthemum plant of the variety substantially as herein shown and described.

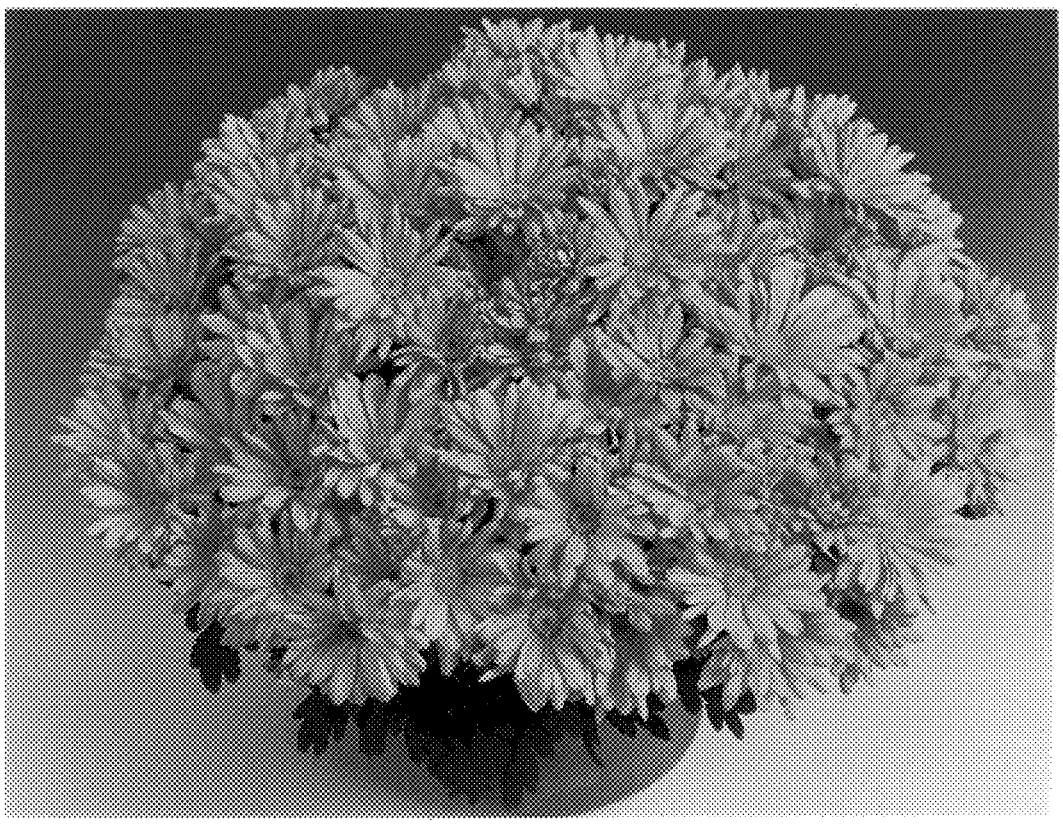

* * * * *